United States Patent
Govari et al.

(10) Patent No.: US 9,320,447 B2
(45) Date of Patent: Apr. 26, 2016

(54) DYNAMIC CANCELLATION OF MRI SEQUENCING NOISE APPEARING IN AN ECG SIGNAL

(71) Applicant: BIOSENSE WEBSTER (ISRAEL) LTD., Yokneam (IL)

(72) Inventors: Assaf Govari, Haifa (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 287 days.

(21) Appl. No.: 14/174,951

(22) Filed: Feb. 7, 2014

(65) Prior Publication Data
US 2015/0223717 A1 Aug. 13, 2015

(51) Int. Cl.
*A61B 5/055* (2006.01)
*A61B 5/0432* (2006.01)
*A61B 5/00* (2006.01)
*A61B 5/04* (2006.01)
*A61B 5/0408* (2006.01)
*A61B 5/042* (2006.01)
*G01R 33/567* (2006.01)

(52) U.S. Cl.
CPC ........... *A61B 5/0432* (2013.01); *A61B 5/04017* (2013.01); *A61B 5/055* (2013.01); *A61B 5/7203* (2013.01); *A61B 5/042* (2013.01); *A61B 5/04087* (2013.01); *G01R 33/5673* (2013.01)

(58) Field of Classification Search
CPC ............................... A61B 5/055; A61B 5/7203
See application file for complete search history.

(56) References Cited

U.S. PATENT DOCUMENTS

| | | | |
|---|---|---|---|
| 4,991,580 | A | 2/1991 | Moore |
| 4,991,587 | A | 2/1991 | Blakeley et al. |
| 5,391,199 | A | 2/1995 | Ben-Haim |
| 5,443,489 | A | 8/1995 | Ben-Haim |
| 5,558,091 | A | 9/1996 | Acker |
| 5,944,022 | A | 8/1999 | Nardella |
| 5,983,126 | A | 11/1999 | Wittkampf |
| 6,070,097 | A | 5/2000 | Kreger |

(Continued)

FOREIGN PATENT DOCUMENTS

| | | |
|---|---|---|
| EP | 0470764 A2 | 2/1992 |
| EP | 1872715 A1 | 1/2008 |

(Continued)

OTHER PUBLICATIONS

European Search Report received Jul. 6, 2015 for Application No. EP15154097.

*Primary Examiner* — Peter Luong
(74) *Attorney, Agent, or Firm* — Notaro, Michalos & Zaccaria P.C.

(57) ABSTRACT

A method, consisting of, while imaging a patient using an initial magnetic resonance imaging (MRI) sequence, receiving an initial set of electrocardiograph (ECG) signals from the patient. The method includes identifying initial noise in the initial set of ECG signals arising from the initial MRI sequence, and characterizing the initial noise in terms of frequency components thereof. The method further includes generating a relation between parameters defining the initial MRI sequence and the frequency components, computing a filter by applying the relation to the parameters of a subsequent MRI sequence, and applying the computed filter to reduce noise in a further set of ECG signals, received from the patient, while imaging the patient using the subsequent MRI sequence.

30 Claims, 6 Drawing Sheets

(56) References Cited

U.S. PATENT DOCUMENTS

| | | |
|---|---|---|
| 6,172,499 B1 | 1/2001 | Ashe |
| 6,177,792 B1 | 1/2001 | Govari |
| 6,456,864 B1 | 9/2002 | Swanson |
| 6,690,963 B2 | 2/2004 | Ben-Haim |
| 6,788,967 B2 | 9/2004 | Ben-Haim |
| 7,039,455 B1 | 5/2006 | Brosovich |
| 7,286,871 B2 | 10/2007 | Cohen |
| 8,626,266 B1 * | 1/2014 | Frank .................... A61B 5/055 600/413 |

FOREIGN PATENT DOCUMENTS

| | | |
|---|---|---|
| EP | 1 872 715 B1 | 5/2009 |
| WO | WO 2012/170119 A1 | 12/2012 |

* cited by examiner

DYNAMIC CANCELLATION OF MRI SEQUENCING NOISE APPEARING IN AN ECG SIGNAL

CROSS-REFERENCE TO RELATED APPLICATION

This application is related to U.S. patent application entitled "Analog Cancellation of MRI Sequencing Noise Appearing in an ECG Signal," filed on even date, which is assigned to the assignees of the present invention, and which is incorporated herein by reference.

FIELD OF THE INVENTION

The present invention relates generally to electrocardiograph (ECG) signals, and specifically to detecting the ECG signals during a magnetic resonance imaging (MRI) procedure.

BACKGROUND OF THE INVENTION

Magnetic resonance imaging (MRI) is an extremely powerful technique for visualizing tissue, particularly soft tissue, of a patient. The technique relies on exciting nuclei, typically hydrogen nuclei, from their equilibrium state, and measuring the resonant radio-frequency signals emitted by the nuclei as they relax back to equilibrium.

In an MRI procedure the cardiac condition of a patient placed in the rapidly changing magnetic fields generated by the procedure may need to be assessed. Monitoring of an electrocardiograph (ECG) signal is a good indicator of the cardiac condition of the patient, so that ECG monitoring may enhance the efficacy of the procedure.

U.S. Pat. No. 7,039,455, to Brosovich, et al., whose disclosure is incorporated herein by reference, describes apparatus for improving the quality of ECG signals obtained from a patient undergoing MRI. The apparatus includes the arrangement of a differential amplifier, a prefilter, a signal limiter circuit and an intermediate amplifier with an integral low pass filter.

U.S. Pat. No. 7,286,871, to Cohen, whose disclosure is incorporated herein by reference, describes a method of reducing contamination of electrical signals recorded in the presence of repeated interference contamination The electrical signal is digitized, the digitizing beginning with a timing signal. A plurality of digitized electrical signals is analyzed, and the electrical signals are synchronized with respect to the timing signal, to obtain an estimated contaminating signal that is subtracted from the digitized electrical signal.

U.S. Pat. No. 4,991,580, to Moore, whose disclosure is incorporated herein by reference, describes a method for improving the quality of ECG signals obtained from a patient undergoing MRI. The method includes conducting the ECG signals having MRI induced noise signals to the input of a slew rate limiter (SRL) circuit having a preselected maximum slew rate. The output of the SRL circuit is connected to a low pass filter circuit.

U.S. Pat. No. 6,070,097, to Kreger, et al., whose disclosure is incorporated herein by reference, describes a method for generating a gating signal for cardiac MRI. An MRI system includes a detector system which receives an ECG signal from a patient being scanned and produces the gating signal. The gating signal is produced when a detected peak in the ECG signal meets a set of R-wave criteria.

European Patent 1,872,715, to Uutela Kimmo, whose disclosure is incorporated herein by reference, describes reference data indicative of statistical properties of biosignal artifacts that is generated by a turbulent electromagnetic environment and that is collected. Multiple channels of the biosignal of the patient are measured in the turbulent electromagnetic environment. Artifacts in the multiple channels are detected using the reference data and parameters are derived for a linear combination of the multiple channels. A refined biosignal is obtained by applying a linear combination to desired signal samples of the multiple channels, the linear combination being defined by the parameters derived.

PCT application WO/2012/170119, to Schweitzer et al., whose disclosure is incorporated herein by reference, describes a system for tracking catheter electrode locations with the body of a patient during an MRI scan sequence The system includes mitigation logic configured to identify one or more impedance measurements that were taken during potentially noise-inducing conditions, and were thus subject to corruption by noise. The mitigation logic is configured to replace the potentially corrupt impedance measurements with previously-obtained impedance measurements taken from an immediately preceding acquisition cycle.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

while imaging a patient using an initial magnetic resonance imaging (MRI) sequence, receiving an initial set of electrocardiograph (ECG) signals from the patient;

identifying initial noise in the initial set of ECG signals arising from the initial MRI sequence;

characterizing the initial noise in terms of frequency components thereof;

generating a relation between parameters defining the initial MRI sequence and the frequency components;

computing a filter by applying the relation to the parameters of a subsequent MRI sequence; and applying the computed filter to reduce noise in a further set of ECG signals, received from the patient, while imaging the patient using the subsequent MRI sequence.

In a disclosed embodiment identifying the initial noise includes generating a reference set of ECG signals prior to imaging the patient, and comparing the initial set of ECG signals with the reference set.

In a further disclosed embodiment characterizing the initial noise includes performing a Fourier transform on the initial noise.

In a yet further disclosed embodiment the parameters defining the initial MRI sequence include variables describing voltage and magnetic field pulses of the initial MRI sequence. Typically, generating the relation includes varying values of the variables while using the initial MRI sequence, and comparing changes in the values with changes in amplitudes of the frequency components.

In an alternative embodiment the initial MRI sequence and the subsequent MRI sequence include a common MRI sequence having common parameters. Typically, the common parameters include variables describing voltage and magnetic field pulses of the common MRI sequence, and the variables have different values for the initial MRI sequence and the subsequent MRI sequence.

In a further alternative embodiment computing the filter includes calculating an expected noise in terms of expected amplitudes of the frequency components, and applying the computed filter includes subtracting the expected amplitudes from amplitudes of corresponding frequencies associated with the further set of ECG signals.

The ECG signals may consist of internal ECG signals acquired from a probe located within the patient. Alternatively or additionally, the ECG signals may consist of external ECG signals acquired from skin of the patient.

The initial and subsequent MRI sequences may include a common plurality of phases, and generating the relation may consist of generating a phase-relation between parameters defining a selected phase of the initial MRI sequence and the frequency components, and computing the filter may consist of computing the filter by applying the phase-relation to the parameters of the selected phase of the subsequent MRI sequence.

In a yet further alternative embodiment the initial set of ECG signals are generated on multiple ECG leads connected to the patient, and identifying the initial noise includes summing signals on the multiple leads.

Typically, identifying the initial noise includes identifying the initial noise using a reference ECG signal acquired prior to imaging the patient.

Alternatively or additionally, identifying the initial noise includes identifying the initial noise during imaging of the patient.

Further alternatively or additionally, identifying the initial noise includes identifying the initial noise using ECG signals from stationary electrodes coupled to the patient.

There is further provided, according to an embodiment of the present invention, apparatus, including:

one or more electrodes, configured to acquire an initial set of electrocardiograph (ECG) signals from a patient; and a processor which is configured to:

receive the initial set of electrocardiograph (ECG) signals from the patient, while imaging the patient using an initial magnetic resonance imaging (MRI) sequence;

identify initial noise in the initial set of ECG signals arising from the initial MRI sequence;

characterize the initial noise in terms of frequency components thereof;

generate a relation between parameters defining the initial MRI sequence and the frequency components;

compute a filter by applying the relation to the parameters of a subsequent MRI sequence; and apply the computed filter to reduce noise in a further set of ECG signals, received from the patient, while imaging the patient using the subsequent MRI sequence.

The present invention will be more fully understood from the following detailed description of the embodiments thereof, taken together with the drawings in which:

DETAILED DESCRIPTION OF EMBODIMENTS

Overview

An embodiment of the present invention provides a noise cancelling system which operates while a magnetic resonance imaging (MRI) procedure is being performed on a patient. During the MRI procedure, electrocardiograph (ECG) signals, acquired using intracardiac and/or skin electrodes, are received from the patient. The MRI procedure injects noise into the acquired ECG signals, and the system reduces or eliminates this noise.

Typically, in a training section of the system a processor stores a reference set of ECG signals that are generated while the MRI procedure is not being performed. ECG signals are then acquired while a selected MRI sequence is being performed, and the processor uses the reference set to identify the injected noise. The processor characterizes the noise in terms of its frequency components, and generates a relation between the frequency components and parameters, and variables associated with the parameters, defining the selected MRI sequence. Typically the noise is characterized, and a respective relation is generated, for multiple different MRI sequences, by operating each of the MRI sequences in turn, and identifying the noise for each different sequence.

In an operational section of the system, the processor selects the relation for a given MRI sequence being used during a procedure, and from the relation computes a noise filter for use when the given MRI sequence is being applied to the patient. The filter is applied to the ECG signals received during application of the given MRI sequence, so as to reduce, or even eliminate, noise in the received ECG signals.

By characterizing the noise in terms of frequency components, and relating these to parameters of a specific MRI sequence, embodiments of the present invention are able to generate respective different noise filters for each different MRI sequence used during an MRI procedure.

While some embodiments of the present invention may generate a noise filter for a complete MRI sequence, other embodiments may generate respective, different, noise filters for separate individual phases of a given MRI sequence.

DETAILED DESCRIPTION

Figure 1:
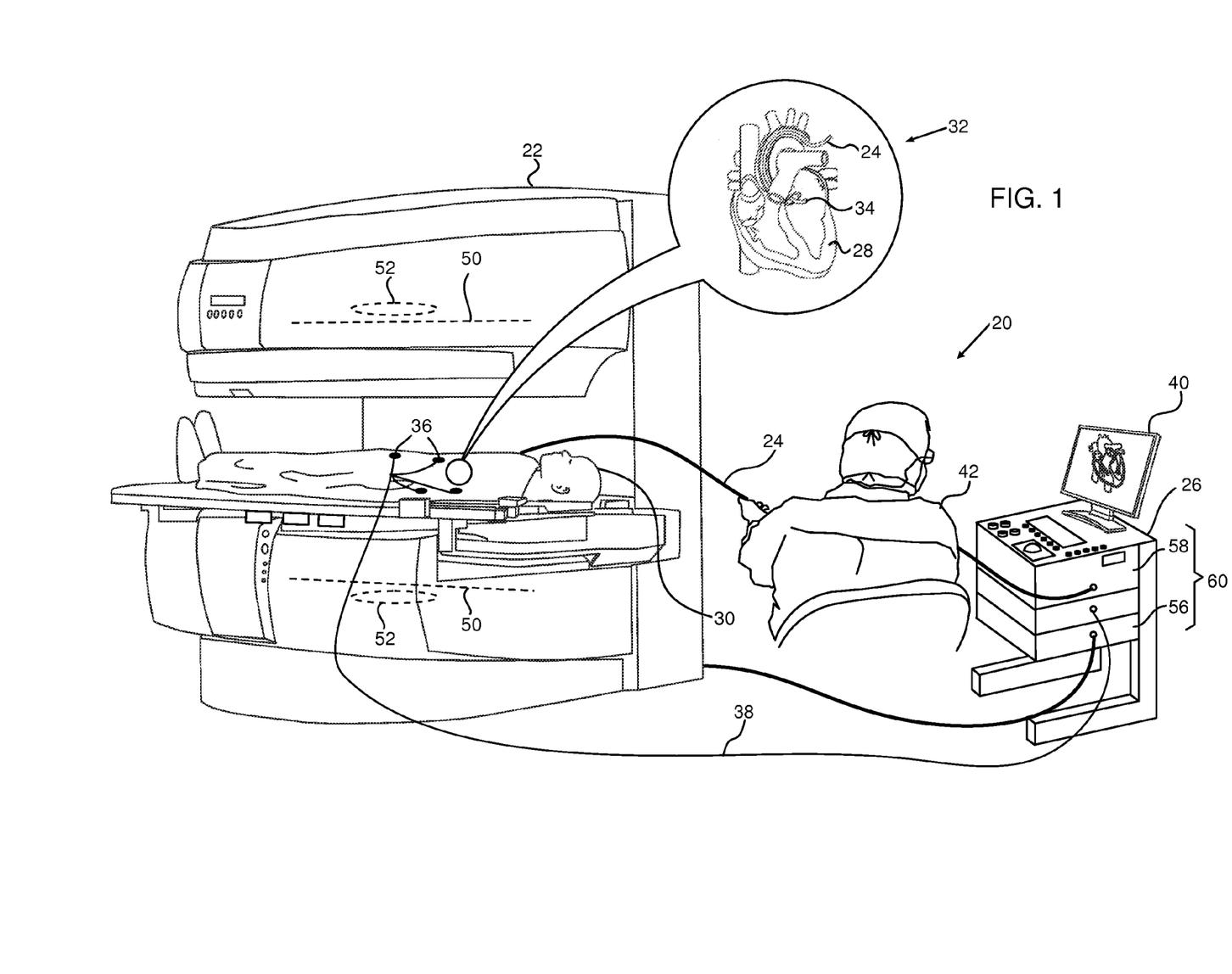
FIG. 1 is a schematic, pictorial illustration of a system for dynamic cancellation of magnetic resonance imaging (MRI) noise appearing in electrocardiograph (ECG) signals, according to an embodiment of the present invention.

Reference is now made to FIG. 1, which is a schematic, pictorial illustration of a system 20 for dynamic cancellation of magnetic resonance imaging (MRI) sequencing noise appearing in electrocardiograph (ECG) signals, according to an embodiment of the present invention. System 20 comprises an MRI scanner 22, a probe 24, such as a catheter, and a control console 26. Probe 24 may be used for acquiring ECG signals in a chamber of a heart 28 of a patient 30, using one or more electrodes 32 in a distal end 34 of the probe.

Signals acquired by electrodes 32 are herein termed internal ECG signals. In some embodiments, probe 24 may be used for additional purposes, such as for performing cardiac ablation. Further alternatively, probe 24 may be used, mutatis mutandis, for other therapeutic and/or diagnostic functions in the heart or in other body organs. The internal ECG signals acquired by electrodes 32 are transferred, typically by conductors and/or optical fibers in probe 24, to control console 26, wherein the signals may be analyzed.

In addition to acquiring internal ECG signals using probe 24, system 20 typically also acquires ECG signals from the skin of patient 30, typically by placing a number of conductive patches 36 on the skin of the patient. Signals acquired by patches 36 are herein termed external ECG signals. External ECG signals are conveyed via a cable 38 to control console 26, which analyzes the signals. Results derived from the analysis may be presented on a display 40 to an operator 42 of system 20.

Operator 42, typically a cardiologist, inserts probe 24 through the vascular system of patient 30 so that distal end 34 of the probe enters a body cavity, herein assumed to be the cardiac chamber from where the internal ECG signals are acquired. Typically the distal end of the probe is tracked by a method known in the art. Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are also incorporated herein by reference.

MRI scanner 22 comprises magnetic field coils 50, including field gradient coils, which together generate a spatially variant magnetic field B(x,y,z). The spatially variant magnetic field provides spatial localization for radio frequency (RF) signals generated in the scanner. In addition, the scanner comprises transmit/receive coils 52. In a transmit mode coils 52 radiate RF pulsed energy to patient 30, the RF pulses of energy interacting with the nuclear spins of the patient's tissue and thereby realigning the magnetic moments of the nuclei away from their equilibrium positions. In a receive mode, coils 52 detect RF signals received from the patient's tissue as the tissue nuclei relax to their equilibrium state. The frequency of the signals generated by the relaxation of nuclei in a given region, the Larmor frequency, is directly proportional to the magnetic field at the region, with a constant of proportionality given by the gyromagnetic ratio γ of the nuclei. Thus, for hydrogen nuclei, equation (1) applies:

$$f(x, y, z) = \frac{\gamma}{2\pi} \cdot B(x, y, z) \quad (1)$$

where f(x,y,z) is the frequency radiated by the relaxing hydrogen nuclei from a point (x,y,z), B(x,y,z) is the magnetic field at the point, and $$\frac{\gamma}{2\pi}$$

is equal to approximately 42.6 MHz·T$^{-1}$.

In some embodiments, scanner 22 is operated by a scanner processor 56, and the ECG signals described above, and the tracking of the probe acquiring the internal ECG signals, are analyzed and controlled by an ECG processor 58. For simplicity, in the description herein a single processor 60 in console 26 is assumed to operate system 20, and those having ordinary skill in the art will be able to adapt the description in the event that more than one processor operates the system.

Thus, in addition to analyzing the ECG signals referred to above, and tracking the probe generating the internal ECG signals, processor 60 operates scanner 22 by using circuitry to control coils 50, including forming required magnetic field gradients, as well as other circuitry to operate transmit/receive coils 52.

Processor 60 typically comprises a general-purpose computer, which is programmed in software to carry out the functions that are described herein. The software may be downloaded to processor 60 in electronic form, over a network, for example, or it may be provided on non-transitory tangible media, such as optical, magnetic or electronic memory media. Alternatively, some or all of the functions of processor 60 may be carried out by dedicated or programmable digital hardware components, or by using a combination of hardware and software elements.

Figure 2:
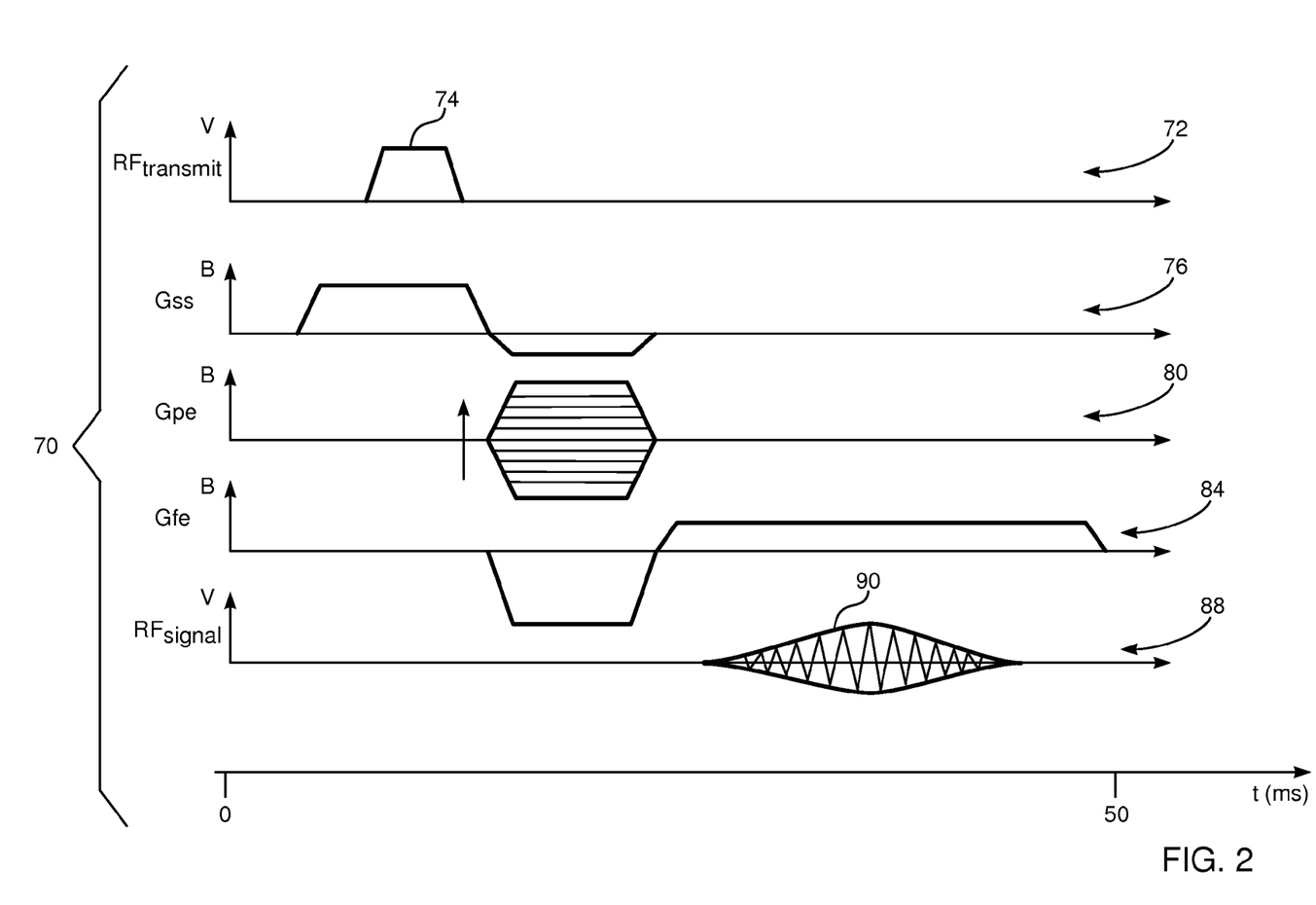
FIG. 2 is a set of voltage vs. time and magnetic field vs. time graphs schematically illustrating a sequence of MRI signals generated during an MRI procedure, according to an embodiment of the present invention.

FIG. 2 is a first set of voltage (V) vs. time (t) and magnetic field (B) vs. time (t) graphs schematically illustrating a sequence 70 of MRI signals generated during an MRI procedure, according to an embodiment of the present invention. A first voltage vs. time graph 72 illustrates a transmit RF pulse 74, generated by coils 52, which is transmitted at the start of sequence 70. The transmit RF pulse length is typically of the order of 2 ms, although it may be larger or smaller than this. Encompassing the transmit RF pulse, illustrated in a first magnetic field vs. time graph 76, is a slice selection gradient (Gss) magnetic field pulse generated by coils 50. The slice selection gradient field identifies a volume of interest in patient 30 that is to be imaged by scanner 22.

A second magnetic field vs. time graph 80 illustrates a phase encoding gradient (Gpe) field pulse, which selects a vertical position of points within the volume of interest. A third magnetic field vs. time graph 84 illustrates a frequency encoding gradient (Gfe) field pulse, which selects a horizontal position of points within the volume of interest.

A second voltage vs. time graph 88 illustrates a receive RF pulse 90, corresponding to the data acquisition signal received by coils 52 in response to the transmit RF pulse.

A typical time between the center of the RF transmit pulse and the center of the RF receive pulse may be approximately 30 ms. A typical time for the overall sequence may be approximately 40 ms. However, the actual times may be larger or smaller than these values.

During the course of an MRI procedure, the sequence of RF pulses and magnetic field settings, illustrated by sequence 70, may be repeated, typically at a repetition rate of the order of 1 s. At each repetition of sequence 70, one or more of the variables defining the magnetic field pulses may be varied, typically so that different regions of patient 36 may be scanned. In some cases, as sequence 70 is repeated, variables of RF transmit pulse 74, such as its amplitude, frequency, or phase, may be changed.

Sequence 70 illustrates one type of MRI sequence, termed a gradient echo sequence, that is typically used in an MRI procedure.

Figure 3:
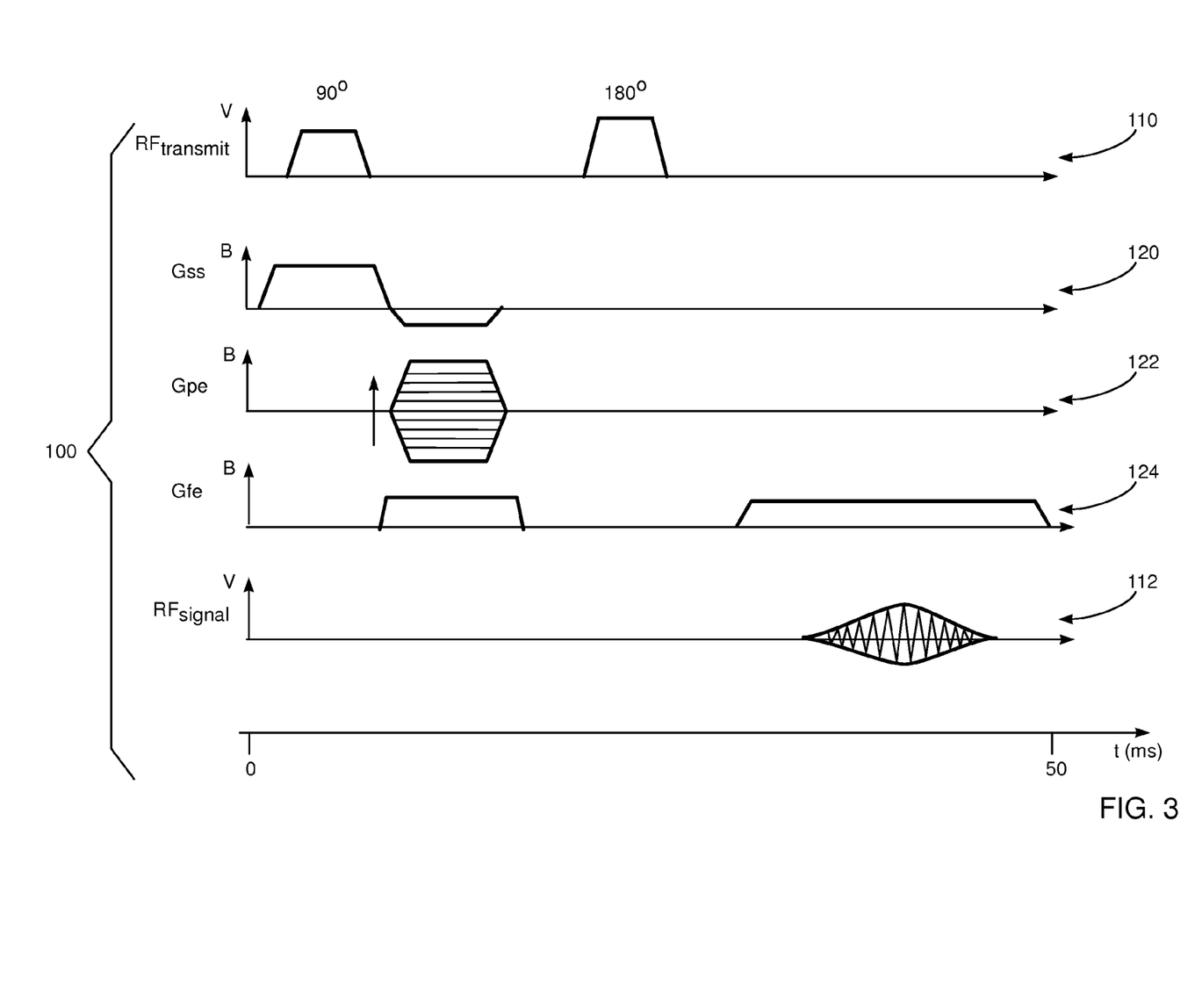
FIG. 3 is an alternative set of voltage vs. time and magnetic field vs. time graphs schematically illustrating a sequence of MRI signals generated during an MRI procedure, according to an embodiment of the present invention.

FIG. 3 is a second set of voltage vs. time and magnetic field vs. time graphs schematically illustrating a sequence 100 of MRI signals generated during an MRI procedure, according to an embodiment of the present invention. As for sequence 70, sequence 100 comprises transmit and receive voltage vs. time graphs 110 and 112, and three magnetic field vs. time graphs 120, 122, and 124. As is illustrated in the graphs, sequence 100 uses two RF transmit pulses and two magnetic field Gfe pulses (in contrast to the one RF pulse and one Gfe pulse of sequence 70). Sequence 100 illustrates a spin echo sequence, that may typically also be used in an MRI procedure.

FIGS. 2 and 3 illustrate two types of MRI sequence that may be used in embodiments of the present invention. Variations on these sequences, as well as other possible sequences, will be apparent to those having ordinary skill in the art, and all such sequences are assumed to be within the scope of the present invention. In the following description, an identifier "m" is used to label each type of MRI sequence, and by way of example the MRI sequence illustrated by FIG. 2 is assumed to have identifier m=1, and the MRI sequence illustrated by FIG. 3 is assumed to have identifier m=2.

FIGS. 2 and 3 also illustrate that each MRI sequence is comprised of a number of phases, corresponding to the different pulses that are generated for the sequence. A phase of an MRI sequence may be defined in terms of a pulse, a number of pulses, and/or parts of a pulse. For example, a selected phase of the MRI sequence of FIG. 2 may be defined as the duration of the Gpe pulse; for the MRI sequence of FIG. 3, another selected phase may be defined as the duration of a first half of the second Gfe pulse.

In general, any MRI sequence may be defined in terms of the variables describing each of the pulses graphed in FIGS. 2 and 3. Thus, referring to voltage vs. time graphs 72 and 112, the variables comprise the frequency, phase, and amplitude of the voltage of the RF pulse initiating a sequence, changes in values of these variables over time, variables of any subsequent RF pulses, and timing of the subsequent RF pulses with respect to the initial RF pulse. Referring to magnetic field vs. time graphs 76, 80, and 84, and graphs 120, 122, and 124, the variables include those describing the shape of the magnetic field pulses, i.e., the amplitude of the field as it varies in time, and timing of the magnetic field pulses with respect to the RF pulse or pulses in graphs 72 and 112, and with respect to each other.

More specifically, each MRI sequence m may be characterized broadly in terms of a set of parameters, each parameter corresponding to one of the pulses of the sequence. In the following description, the set of parameters for an MRI sequence m is written as $\{S\}_m$.

For example, MRI sequence m=1, illustrated in FIG. 2, may have a set of parameters $\{S\}_1 = \{P_{RF}, P_{Gss}, P_{Gpe}, P_{Gfe}, P_{signal}\}$, each of the elements of the set representing a voltage or a magnetic field pulse. In contrast, MRI sequence m=2, illustrated in FIG. 3, has a set of parameters $\{S\}_2 = \{P_{RF1}, P_{RF2}, P_{Gss}, P_{Gpe}, P_{Gfe1}, P_{Gfe2}, P_{signal}\}$.

For any given MRI sequence m, there is a further, more detailed, characterization of each of the parameters in the set. Thus, referring to voltage vs. time graph 72 of m=1, parameter $P_{RF}$ is characterized in terms of the variables frequency f, phase φ, and amplitude A of the voltage of the RF pulse initiating a sequence, and changes in values of these variables over time t. $P_{RF}$ may thus be represented as a set of ordered 4-tuples, which may be written as an equation (2):

$$P_{RF} \equiv \{(f, \emptyset, A, t)\}_1 \quad (2)$$

where the set subscript is the identifier m of the sequence.

Similarly, referring to magnetic field Gss vs. time graph 76 of m=1, parameter $P_{Gss}$ is characterized in terms of the variable magnetic field B at time t, so that $P_{Gss}$ may be represented as a set of ordered pairs of variables, which may be written as an equation (3):

$$P_{Gss} \equiv \{(B, t)\}_1 \quad (3)$$

Referring to voltage vs. time graph 110 of m=2, parameters $P_{RF1}$ and $P_{RF2}$ may be represented by the equations:

$$P_{RF1} \equiv \{(f_1, \emptyset_1, A_1, t)\}_2 \quad (4)$$

and $$P_{RF2} \equiv \{(f_2, \emptyset_2, A_2, t)\}_2 \quad (5)$$

where $f_1$, $\phi_1$, $A_1$ are the frequency, phase and amplitude variables at time t of the first pulse of m=2, and $f_2$, $\phi_2$, $A_2$ are the frequency, phase and amplitude variables at time t of the second pulse of m=2.

As another example, referring to field vs. time graph 124, parameters $P_{Gfe1}$, $P_{Gfe2}$ may be represented by the equations:

$$P_{Gfe1} \equiv \{(B_1, t)\}_2 \quad (6)$$

and $$P_{Gfe2} \equiv \{(B_2, t)\}_2 \quad (7)$$

where $B_1$ and $B_2$ are the field variables of the first Gfe pulse and the second Gfe pulse at time t.

Prior to operating scanner 22, operator 42 uses processor 60 to store $\{S\}_m$, in terms of its parameters and the variables associated with each parameter (in the broad and more detailed manner described above) for each MRI sequence m. During a procedure where scanner 22 is operated, the processor recalls the parameters and variables of $\{S\}_m$ as is explained with reference to the flowchart of FIG. 4.

Figure 4:
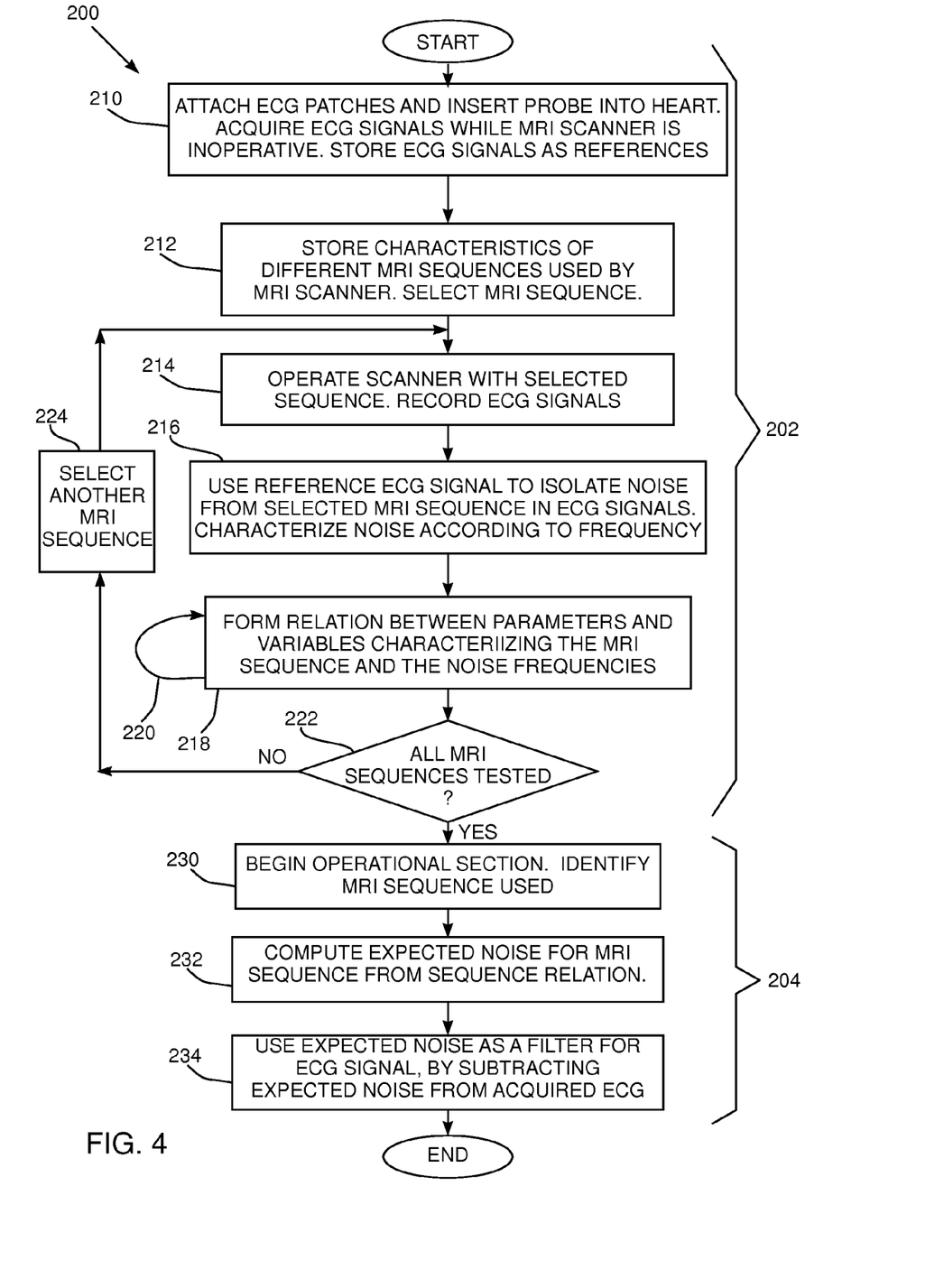
FIG. 4 is a flowchart of steps performed in implementing the system of FIG. 1, according to an embodiment of the present invention.

FIG. 4 is a flowchart 200 of steps performed in implementing system 20, according to an embodiment of the present invention. The flowchart is divided into two sections: a training section 202 and an operational section 204. The description of the flowchart assumes that appropriate steps of the flowchart are implemented using single processor 60. If system 20 comprises scanner processor 56 and ECG processor 58, then the flowchart steps may be assumed to be implemented by ECG processor 58, using communications as to the timing and identity of MRI sequence m from scanner processor 56.

In an initial step 210 of the training phase, operator 42 attaches patches 36 to patient 30, and inserts probe 24 into heart 28 of the patient. Patches 36 acquire external ECG signals, and the electrode or electrodes of probe 24 acquire internal ECG signals, while scanner 22 is inoperative. Processor 60 receives the acquired ECG signals, and stores a selected group of the signals as a reference set of signals.

Typically, the reference set of signals comprises signals from electrodes which are relatively stationary with respect to patient 30. For example, the reference set of signals may be from patches 36. In some embodiments probe 24 may be stationary, e.g., if it is being used as an internal reference probe in heart 28, in which case other movable probes (not shown in FIG. 1) may be inserted into heart 28. If probe 24 is stationary, then signals from its electrode or electrodes may be used as ECG reference signals. In some embodiments the reference set may comprise a sub-set of patch signals, such as a selected one of the signals from the patches, and/or a sub-set of signals from electrodes of probe 24 if the probe is stationary.

In a characterization step 212, the processor stores the parameters and the variables of the different MRI sequences to be used in operating system 20. In other words, the processor stores the sets $\{S\}_m$ for each value of m to be used in the procedure. Once the parameters and the variables have been stored the processor selects an MRI sequence m with which to operate the scanner.

In a recording step 214, scanner 22 is operated using the selected MRI sequence, and the processor acquires and records ECG signals, from patches 36 and from the electrodes of probe 24, generated while the scanner operates. The recorded ECG signals are selected to correspond with, i.e., to be on the same leads as, the reference signals stored in step 210. The recorded ECG signals include noise, injected, inter alia, into the leads conveying the signals, because of the scanner operation. The scanner operation is typically for a multiplicity of scans of the sequence, although there is no requirement for this, and the operation may be for single scan of the sequence.

In a noise isolation step 216, the recorded ECG signals of step 214 are compared with the reference set of ECG signals stored in step 210. Using the comparison, processor 60 isolates the noise signal that is generated. The processor then characterizes the generated noise according to frequency, typically by applying a Fourier transform to the noise signal, so deriving a set of frequencies and associated frequency amplitudes for the noise signal.

The set of frequencies and associated frequency amplitudes of the noise generated by MRI sequence m is denoted herein by the symbol $\{N\}_m$, which may be written as:

$$\{N\}_m \equiv \{(f_i, A_i)\}_m \tag{8}$$

where $A_i$ is the amplitude of frequency $f_i$, and i is an identifier of the frequency.

In a relation forming step 218, the processor generates a relation between the set $\{N\}_m$ derived in step 216 and the set $\{S\}_m$ stored in step 212. The relation is typically generated by varying one or more of the variables of each of the parameters of $\{S\}_m$, as represented by an arrow 220 in the flowchart, for the selected MRI sequence being analyzed. The variation of a particular variable provides information to the processor regarding the effect of the variable on each of frequencies in the set of frequencies of step 216.

The generated relation may be denoted by the equation:

$$\{N\}_m = [M]_m \cdot \{S\}_m \tag{9}$$

where $[M]_m$ is a matrix relating the noise on the ECG signal to the MRI sequence m.

In a decision step 222, the processor checks if all MRI sequences have been analyzed. If a sequence remains, the flowchart proceeds to step 224 to select another MRI sequence, and then returns to step 214. If all sequences have been analyzed, training section 202 concludes and operational section 204 begins.

In a first step 230 of the operational section, the processor identifies the MRI sequence m being used. The processor also determines the specific numerical values of $\{S\}_m$ being used for the sequence. The numerical values are herein termed $\{S_p\}_m$, subscript p indicating numerical values.

In a noise prediction step 232, the numerical values of step 230 are used to determine numerical values $\{N_p\}_m$ of the noise expected on the ECG signal. The determination uses matrix $[M]_m$ from step 218, according to the equation:

$$\{N_p\}_m = [M]_m \cdot \{S_p\}_m \tag{10}$$

From equation (8), $\{N_p\}_m$ may be rewritten as:

$$\{N_p\}_m \equiv \{(f_p, A_p)\}_m \tag{11}$$

Equation (11) represents the expected noise, on the ECG signal acquired while MRI sequence m is operative, as a set of ordered pairs of frequency and frequency amplitude.

In a final filtration step 234 of the flowchart, the expected noise represented by equation (11) is used as a noise filter for all the acquired ECG signals. The filtration is performed by performing a Fourier transform on each of the ECG signals received from patches 36 and the electrodes of probe 24, and subtracting the values of $A_p$, as given by equation (11), for each frequency $f_p$ of the respective signal. An inverse Fourier transform is then performed on the result of the subtraction, to regenerate ECG signals from which noise has been removed.

The description above of flowchart 200 assumes that a complete MRI sequence m is being considered, and that noise filter $\{N_p\}_m$, given by equation (11) is used for filtering the ECG signal acquired while the complete sequence is operative. The description of the flowchart may be adapted, mutatis mutandis, for the case that one or more phases of sequence m are analyzed, in which case a separate noise filter may be calculated and applied to respective parts of the ECG signal acquired during each phase.

Thus, for a given phase f of sequence m the set of parameters for the phase of the MRI sequence may be written as $\{S\}_{mf}$. In noise isolation step 216, an equation for the set of frequencies and associated frequency amplitudes of the noise of phase f generated by may be denoted by the symbol $\{N\}_{mf}$, which may be written as:

$$\{N\}_{mf} \equiv \{(f_i, A_i)\}_{mf} \tag{12}$$

The relation for phase f, generated in step 218, may then be written as:

$$\{N\}_{mf} = [M]_{mf} \cdot \{S\}_{mf} \tag{13}$$

where $[M]_{mf}$ is a matrix relating the noise on the ECG signal during phase f to the parameters of phase f of the MRI sequence m.

The noise filter, calculated in step 232, may be written as:

$$\{N_p\}_{mf} = [M]_{mf} \cdot \{S_p\}_{mf} \tag{14}$$

and $$\{N_p\}_{mf} \equiv \{(f_p, A_p)\}_{mf} \tag{15}$$

In step 234, the expected noise represented by equation (15) is used as a noise filter for part of the ECG signal that is acquired during phase f. The filtration may be performed in substantially the same manner as described above for the complete MRI sequence m, i.e., by transforming the relevant part of the ECG signal, subtracting the values of $A_p$, as given by equation (15), and then performing an inverse Fourier transform to regenerate the part of the ECG signal with noise removed.

The description of flowchart 200 has assumed that system 20 is implemented using training section 202 followed by operational section 204. However, in alternative embodiments of the present invention there is no requirement for a separate training section, and in these embodiments the training of system 20 is performed "on-the-fly." The steps of flowcharts 300 and 400, described below with reference to FIGS. 5 and 6, exemplify how system 20 may be implemented during performance of an MRI procedure on a patient, without a separate training section.

Figure 5:
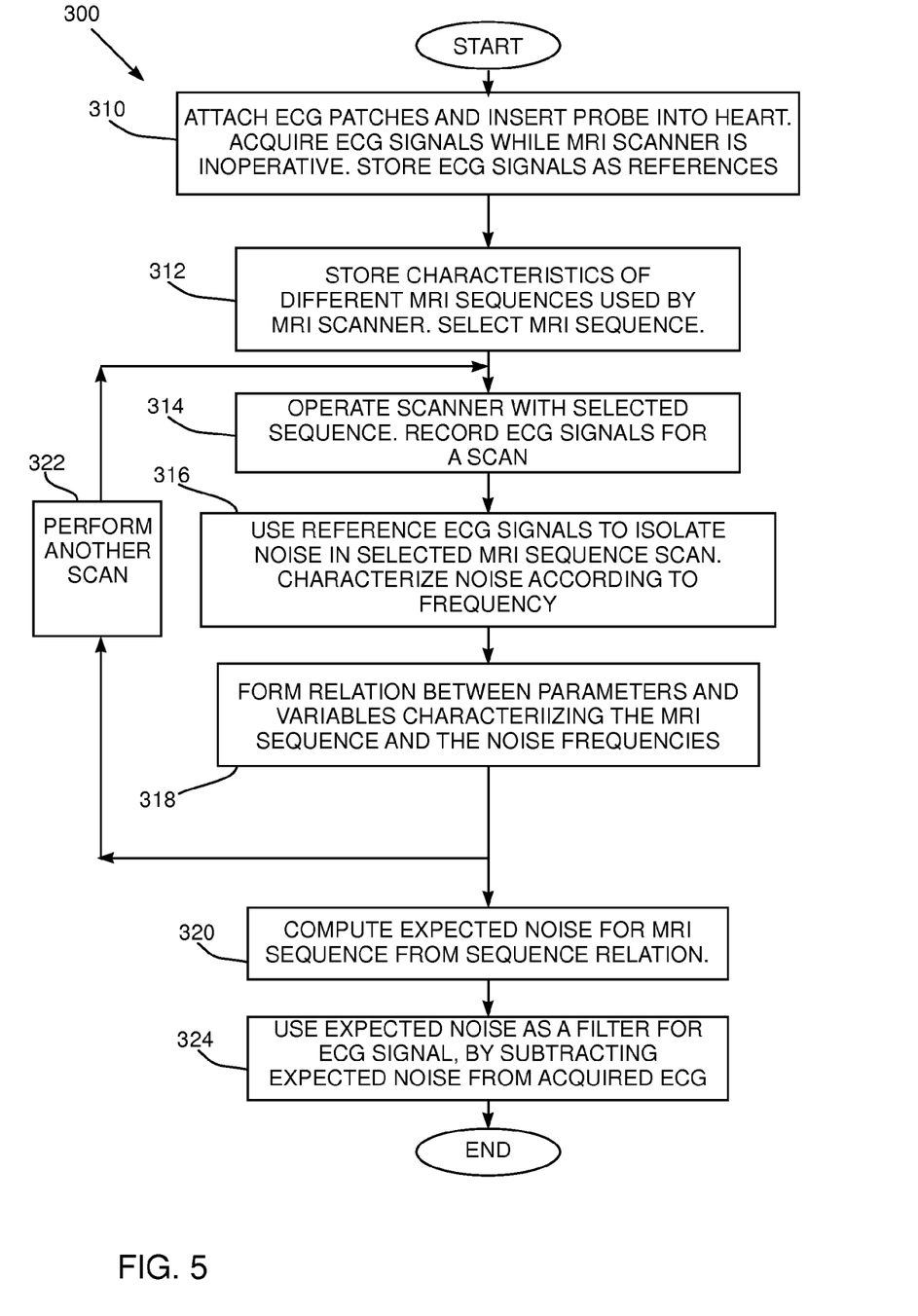
FIG. 5 is a flowchart of steps performed in implementing the system of FIG. 1, according to an alternative embodiment of the present invention.

FIG. 5 is a flowchart 300 of steps performed in implementing system 20, according to an alternative embodiment of the present invention. First and second steps 310 and 312 are substantially as described for steps 210 and 212 of flowchart 200, respectively storing reference ECG signals and MRI sequence characteristics. A recording step 314 is generally the same as step 214, although typically the ECG recording is for a small number of MRI scans, or for a single scan.

A noise isolation step 316 is generally the same as step 216, using the ECG reference signals from step 310 to isolate MRI noise in the ECG signals recorded in step 314.

A relation forming step 318 is also generally the same as step 218, so that the processor generates a relation between the noise frequencies derived in step 316 and the MRI characteristics stored in step 312. The generated relation is given by equation (9) above, and gives an estimate of matrix $[M]_m$.

The flowchart then proceeds, with the estimate of matrix $[M]_m$, to a noise prediction step 320.

Typically, as indicated by an iteration step 322, where the scanner is operated for another scan, steps 314, 316, and 318 are iterated. As the iteration continues, the processor is able to improve the accuracy of matrix $[M]_m$ generated in step 318.

Noise prediction step 320 is generally the same as step 232, the processor using the estimate of matrix $[M]_m$ derived in step 318 to compute an expected noise on the ECG signal, according to equations (10) and (11).

A final filtration step 324 is substantially the same as step 234, the processor subtracting the expected noise (from step 320) from all of the ECG signals, so as to generate ECG signals from which noise has been removed.

Figure 6:
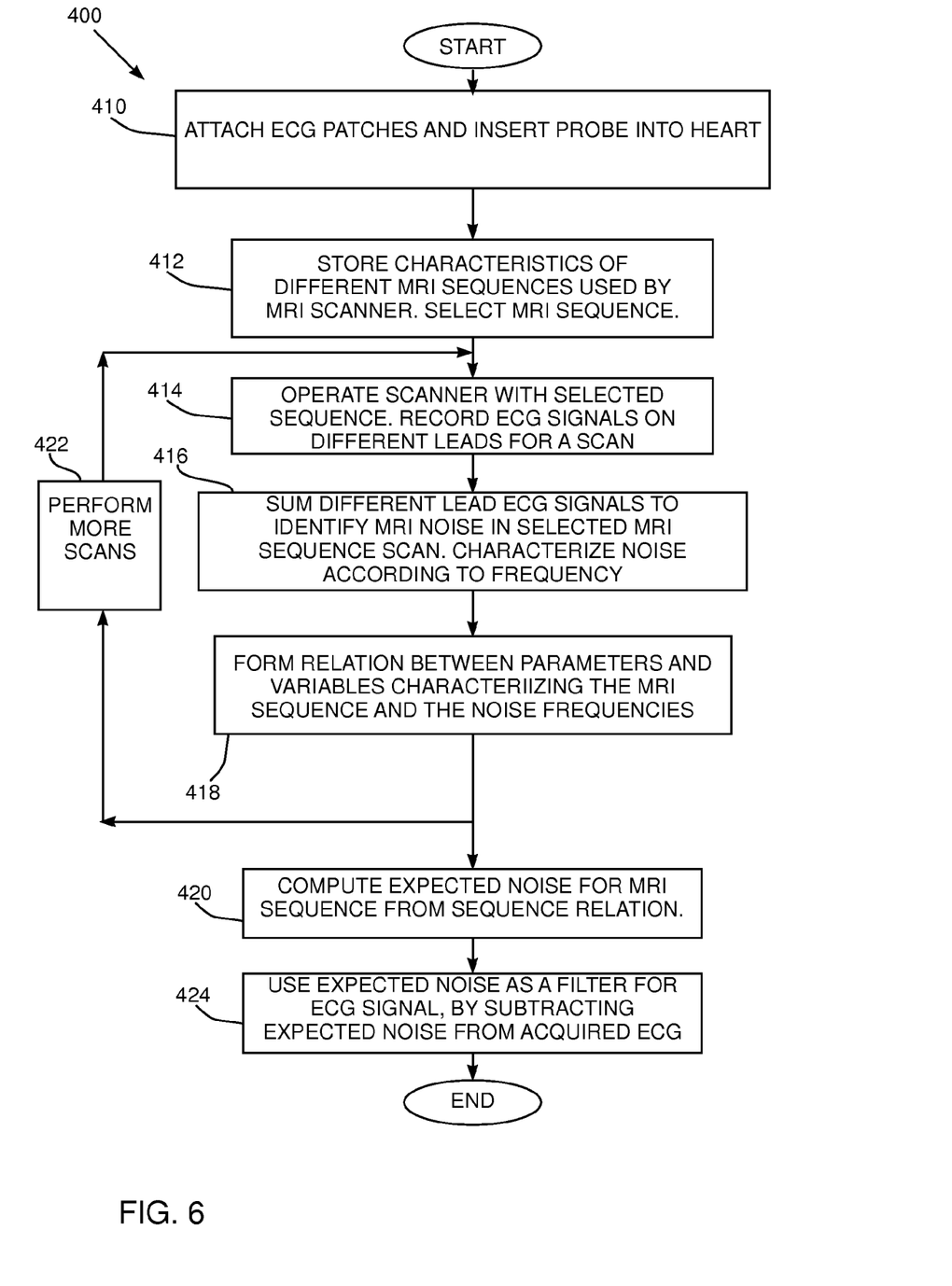
FIG. 6 is a flowchart of steps performed in implementing the system of FIG. 1, according to a further alternative embodiment of the present invention.

FIG. 6 is a flowchart 400 of steps performed in implementing system 20, according to a further alternative embodiment of the present invention. First and second steps 410 and 412 are generally the same as steps 210 and 212, except that in step 410 there is no requirement to acquire ECG signals while the scanner is inoperative, and there is no storage of reference ECG signals.

A recording step 414 is generally the same as step 214. Typically, the recorded ECG signals are those from a multiplicity of leads comprising patches 36 and/or stationary electrodes of probe 24.

In a noise identification step 416, the signals on the multiplicity of leads are summed. The summed signal enables processor 70 to estimate the noise signal generated by the MRI scan. As described above for step 216, the processor characterizes the generated noise, making an estimate of $\{N\}_m$ as given by equation (8).

A relation forming step 418 is generally the same as step 218, so that the processor generates a relation between the estimate of $\{N\}_m$ derived in step 416 and the MRI characteristics stored in step 312. The generated relation is given by equation (9) above, and gives an estimate of matrix $[M]_m$.

The flowchart then proceeds, with the estimate of matrix $[M]_m$, to a noise prediction step 420.

Typically, as indicated by an iteration step 422, where the scanner is operated for more scans, steps 414, 416, and 418 are iterated. As the iteration continues, the processor is able to improve the accuracy of the estimate of matrix $[M]_m$ generated in step 418.

Noise prediction step 420 is generally the same as step 232, the processor using the estimate of matrix $[M]_m$ derived in step 418 to compute an expected noise on the ECG signal, according to equations (10) and (11).

A final filtration step 424 is substantially the same as step 234, the processor subtracting the expected noise (generated in step 420) from all of the ECG signals, so as to generate ECG signals from which noise has been removed.

In the case that two separate processors 56 and 58 are operative, and that ECG processor 58 is used to implement the steps of flowcharts 200, 300, or 400, scanner processor 56 may inform ECG processor 58 of appropriate entities associated with any given MRI sequence, such as the identity of the sequence, start and/or end times of the sequence, and start and/or end times of phases of the sequence.

Flowcharts 300 and 400 describe two different methods for operating system 20 without having a training section first. It will be appreciated that the methods described for the two flowcharts, for estimating the noise introduced into the ECG signals by the MRI scans, may be combined. Such a combination may lead to faster and/or more exact identification of the induced MRI noise, compared to applying the process of just one of the flowcharts.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   while imaging a patient using an initial magnetic resonance imaging (MRI) sequence, receiving an initial set of electrocardiograph (ECG) signals from the patient;
   identifying initial noise in the initial set of ECG signals arising from the initial MRI sequence;
   characterizing the initial noise in terms of frequency components thereof;
   generating a relation between parameters defining the initial MRI sequence and the frequency components;
   computing a filter by applying the relation to the parameters of a subsequent MRI sequence; and
   applying the computed filter to reduce noise in a further set of ECG signals, received from the patient, while imaging the patient using the subsequent MRI sequence.

2. The method according to claim 1, wherein identifying the initial noise comprises generating a reference set of ECG signals prior to imaging the patient, and comparing the initial set of ECG signals with the reference set.

3. The method according to claim 1, wherein characterizing the initial noise comprises performing a Fourier transform on the initial noise.

4. The method according to claim 1, wherein the parameters defining the initial MRI sequence comprise variables describing voltage and magnetic field pulses of the initial MRI sequence.

5. The method according to claim 4, wherein generating the relation comprises varying values of the variables while using the initial MRI sequence, and comparing changes in the values with changes in amplitudes of the frequency components.

6. The method according to claim 1, wherein the initial MRI sequence and the subsequent MRI sequence comprise a common MRI sequence having common parameters.

7. The method according to claim 6, wherein the common parameters comprise variables describing voltage and magnetic field pulses of the common MRI sequence, and wherein the variables have different values for the initial MRI sequence and the subsequent MRI sequence.

8. The method according to claim 1, wherein computing the filter comprises calculating an expected noise in terms of expected amplitudes of the frequency components, and wherein applying the computed filter comprises subtracting the expected amplitudes from amplitudes of corresponding frequencies associated with the further set of ECG signals.

9. The method according to claim 1, wherein the ECG signals comprise internal ECG signals acquired from a probe located within the patient.

10. The method according to claim 1, wherein the ECG signals comprise external ECG signals acquired from skin of the patient.

11. The method according to claim 1, wherein the initial and subsequent MRI sequences comprise a common plurality of phases, and wherein generating the relation comprises generating a phase-relation between parameters defining a selected phase of the initial MRI sequence and the frequency components, and wherein computing the filter comprises computing the filter by applying the phase-relation to the parameters of the selected phase of the subsequent MRI sequence.

12. The method according to claim 1, wherein the initial set of ECG signals are generated on multiple ECG leads connected to the patient, and wherein identifying the initial noise comprises summing signals on the multiple leads.

13. The method according to claim 1, wherein identifying the initial noise comprises identifying the initial noise using a reference ECG signal acquired prior to imaging the patient.

14. The method according to claim 1, wherein identifying the initial noise comprises identifying the initial noise during imaging of the patient.

15. The method according to claim 1, wherein identifying the initial noise comprises identifying the initial noise using ECG signals from stationary electrodes coupled to the patient.

16. Apparatus, comprising:
one or more electrodes, configured to acquire an initial set of electrocardiograph (ECG) signals from a patient; and
a processor which is configured to:
receive the initial set of electrocardiograph (ECG) signals from the patient, while imaging the patient using an initial magnetic resonance imaging (MRI) sequence;
identify initial noise in the initial set of ECG signals arising from the initial MRI sequence;
characterize the initial noise in terms of frequency components thereof;
generate a relation between parameters defining the initial MRI sequence and the frequency components;
compute a filter by applying the relation to the parameters of a subsequent MRI sequence; and
apply the computed filter to reduce noise in a further set of ECG signals, received from the patient, while imaging the patient using the subsequent MRI sequence.

17. The apparatus according to claim 16, wherein identifying the initial noise comprises generating a reference set of ECG signals prior to imaging the patient, and comparing the initial set of ECG signals with the reference set.

18. The apparatus according to claim 16, wherein characterizing the initial noise comprises performing a Fourier transform on the initial noise.

19. The apparatus according to claim 16, wherein the parameters defining the initial MRI sequence comprise variables describing voltage and magnetic field pulses of the initial MRI sequence.

20. The apparatus according to claim 19, wherein generating the relation comprises varying values of the variables while using the initial MRI sequence, and comparing changes in the values with changes in amplitudes of the frequency components.

21. The apparatus according to claim 16, wherein the initial MRI sequence and the subsequent MRI sequence comprise a common MRI sequence having common parameters.

22. The apparatus according to claim 21, wherein the common parameters comprise variables describing voltage and magnetic field pulses of the common MRI sequence, and wherein the variables have different values for the initial MRI sequence and the subsequent MRI sequence.

23. The apparatus according to claim 16, wherein computing the filter comprises calculating an expected noise in terms of expected amplitudes of the frequency components, and wherein applying the computed filter comprises subtracting the expected amplitudes from amplitudes of corresponding frequencies associated with the further set of ECG signals.

24. The apparatus according to claim 16, wherein the one or more electrodes are located within the patient, and wherein the ECG signals comprise internal ECG signals acquired from the one or more electrodes.

25. The apparatus according to claim 16, wherein the one or more electrodes are located on skin of the patient, and wherein the ECG signals comprise external ECG signals acquired from the one or more electrodes.

26. The apparatus according to claim 16, wherein the initial and subsequent MRI sequences comprise a common plurality of phases, and wherein generating the relation comprises generating a phase-relation between parameters defining a selected phase of the initial MRI sequence and the frequency components, and wherein computing the filter comprises computing the filter by applying the phase-relation to the parameters of the selected phase of the subsequent MRI sequence.

27. The apparatus according to claim 16, and comprising multiple ECG leads configured to acquire the initial set of ECG signals, and wherein identifying the initial noise comprises summing signals on the multiple ECG leads.

28. The apparatus according to claim 16, wherein identifying the initial noise comprises identifying the initial noise using a reference ECG signal acquired prior to imaging the patient.

29. The apparatus according to claim 16, wherein identifying the initial noise comprises identifying the initial noise during imaging of the patient.

30. The apparatus according to claim 16, wherein the one or more electrodes comprise stationary electrodes coupled to the patient, and wherein identifying the initial noise comprises identifying the initial noise using ECG signals from the stationary electrodes.

* * * * *